United States Patent [19]

Flury et al.

[11] Patent Number: 4,859,761
[45] Date of Patent: Aug. 22, 1989

[54] CYANOGUANIDINES AS HARDENERS FOR EPOXY RESINS

[75] Inventors: Peter Flury, Himmelried; Alex Alder, Arisdorf, both of Switzerland

[73] Assignee: Ciba-Geigy Corporation, Ardsley, N.Y.

[21] Appl. No.: 238,638

[22] Filed: Aug. 30, 1988

[30] Foreign Application Priority Data

Sep. 2, 1987 [CH] Switzerland .......................... 3359/87

[51] Int. Cl.$^4$ .......................... C08G 59/40; C08G 59/50
[52] U.S. Cl. .................................... 528/123; 525/504; 528/361; 528/407
[58] Field of Search ................ 525/504; 528/123, 361, 528/407

[56] References Cited

U.S. PATENT DOCUMENTS

| | | | |
|---|---|---|---|
| 3,732,286 | 5/1973 | Son et al. | 528/123 X |
| 3,864,313 | 2/1975 | Susman | 528/61 |
| 4,111,909 | 9/1978 | Simons | 528/123 |
| 4,140,658 | 2/1979 | Seltzer | 528/123 X |
| 4,379,728 | 4/1983 | Lin | 528/123 X |
| 4,621,128 | 11/1986 | von Seyerl | 528/123 X |
| 4,705,842 | 11/1987 | von Seyerl | 528/123 X |

FOREIGN PATENT DOCUMENTS 61-207425  9/1986  Japan .

OTHER PUBLICATIONS

H. Lee and K. Neville, "Handbook of Epoxy Resins", McGraw-Hill, N.Y. (1982), pp. 10–16.
Derwent Abstract 85-096311/16.

*Primary Examiner*—Earl Nielsen
*Attorney, Agent, or Firm*—Luther A. R. Hall

[57] ABSTRACT

Curable epoxy resin compositions containing cyanoguanidines of formula I

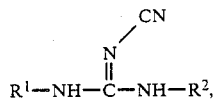

wherein, for example, $R^1$ and $R^2$ are phenyl, as latent hardeners, have good properties and are especially suitable for use as laminating resins.

13 Claims, No Drawings

# CYANOGUANIDINES AS HARDENERS FOR EPOXY RESINS

The present invention relates to curable expoxy resin compositions containing specific cyanoguanidines at latent hardeners and to the use thereof.

Dicyandiamide has long been used with success at latent hardener for epoxy resins (q.v. H. Lee and K. Neville "Handbook of Epoxy Resins", McGraw Hill, New York, 1982, pp. 10-16) and is used in practice in particular as hardener for solid laminating resins. However, dicyandiamide has the serious drawback that it is only soluble in solvents which are unsuitable for the laminating industry, for example in water, acetone/water, methanol, N-methylpyrrolidone, dimethyl formamide, hydroxylated ethers and the like. The solvent commonly used as the present time, 2-methoxyethanol, is problematical for toxicological reasons.

The cyanoguanidines of the compositions of this invention are, like dicyandiamide, latent hardeners which are stable at room temperature, but effect rapid crosslinking of the resins at elevated temperature. They are readily soluble in unproblematical solvents suitable for the application of epoxy resins.

Specifically, the present invention relates to curable compositions containing
(a) an epoxy resin and
(b) as hardener for the epoxy resin, a cyanoguanidine of formula I $$R^1-NH-\underset{\underset{N}{\|}}{C}(-{}^{CN})-NH-R^2, \quad (I)$$

wherein $R^1$ and $R^2$ are each independently of the other $C_1$-$C_{12}$alkyl, $C_2$-$C_{12}$alkenyl, $C_5$-$C_{10}$cycloalkyl, $C_6$-$C_{10}$aryl or $C_7$-$C_{12}$aralkyl, or are a heterocyclic radical of 4 to 8 carbon atoms or a group of formula II $$R-T-\text{(phenyl)} \quad (II)$$

wherein R is phenyl or a heterocyclic radical of 4 to 5 carbon atoms, and T is methylene, isopropylidene, CO, O, S or $SO_2$, which radicals $R^1$ and $R^2$ are unsubstituted or substituted by $C_1$-$C_4$alkyl, $C_1$-$C_4$alkoxy, nitro, halogen, $R^3OCO$ or $R^3COO$, where $R^3$ is phenyl or $C_1$-$C_4$alkyl.

The structure of the cyanoguanidines contained in the compositions of this invention has, for simplicity's sake, been illustrated as 2-cyanoguanidine (i.e. with the cyano group attached to the =N-nitrogen atom). It will be self-evident that these compounds may also be in the form of tautomers, i.e. as 1- or 3-cyanoguanidines, and that the position of equilibrium between the possible tautomers depends on the radicals $R^1$ and $R^2$.

Cyanoguanidines of the type $$\underset{R''}{\overset{R'}{>}}N-\underset{\underset{NH}{\|}}{C}-NHCN$$

are known hardeners for acetal resins or polyurethane resins, js disclosed, for example, in Japanese patent Kokai Sho-60-44543 (1985) and in U.S. Pat. No. 3,864,313. The curable acetal resin compositions disclosed in the above mentioned Japanese patent publication additionally contain small amounts of a polyglycidyl ether or a diglycidyl ester to improve the adhesion of the polyacetal resin and the inorganic fillers present therein.

Japanese patent Kokai Sho-61-207425 (1986) discloses the use of mixtures of cyanoguanidines, in particular dicyandiamide, polyether-polyamines and substituted guanidines as hardeners for special elastomer-modified epoxy resins. These hardener mixtures are not suitable as latent hardeners.

The cyanoguanidines of formula I can be prepared by reacting a carbodiimide of formula III $$R^1-N=C=N-R^2 \quad (III),$$

wherein $R^1$ und $R^2$ are as defined above, with cyanamide.

The radicals $R^1$ and $R^2$ of the cyanoguanidines of formula I may each independently of the other be a straight chain or branched alkyl group of 1 to 12, preferably 1 to 6 and, most preferably, 3 or 4, carbon atoms. Examples of suitable alkyl groups are dodecyl, decyl, octyl, heptyl, butyl, propyl, ethyl or methyl.

$R^1$ and/or $R^2$ as $C_2$-$C_{12}$alkenyl can also be straight chain or branched radicals and the double bond can be in any of the possible positions. Preferred alkenyl groups are those of 2 to 6, in particular 3 or 4, carbon atoms, for example 1-, 2- or 3-butenyl or 1- or 2-propenyl.

$R^1$ and/or $R^2$ as cycloalkyl can be cyclopentyl or, preferably, cyclohexyl. The cycloalkyl radicals can also contain more than one ring, as for example decalinyl.

$R^1$ and/or $R^2$ as aryl are preferably phenyl, substituted phenyl or naphthyl. $C_7$-$C_{12}$Aralkyl may suitably be benzyl or naphthylmethyl.

Heterocyclic radicals $R^1$ and/or $R^2$ are preferably 5- or 6-membered rings containing one or two hetero atoms, preferably N, O or S, and are, for example, monovalent radicals of furan, pyran, pyridine, pyrrole, imidazole, thiophene and the like.

If $R^1$ and/or $R^2$ are a group of formula II, then R is phenyl or a heterocyclic radical, for example one of those mentioned above. T is preferably methylene, isopropylidene or, most preferably, O. The phenylene radical in the group of formula II is preferably 1,4-phenylene.

All the above mentioned radicals $R^1$ and/or $R^2$ may be unsubstituted or may carry one or more, preferably one or two, of the cited substituents. Suitable $C_1$-$C_4$alkyl substituents are methyl, ethyl, n-propyl, isopropyl, n-butyl, isobutyl, sec-butyl or tert-butyl. Suitable $C_1$-$C_4$alkoxy substituents are those which contain the alkyl groups already mentioned.

Examples of suitable halogen substituents are iodine, bromine, fluorine and, preferably, chlorine. Suitable alkoxycarbonyl or alkylcarboxy radicals $R^3OCO$ or $R^3COO$ are those wherein $R^3$ is phenyl or one of the $C_1$-$C_4$alkyl groups cited above, in particular methyl.

It is preferred to use cyanoguanidines in which $R^1$ and $R^2$ are each independently of the other $C_1$-$C_6$alkyl, $C_2$-$C_6$alkenyl, $C_5$-$C_6$cycloalkyl, $C_6$-$C_{10}$aryl, benzyl, or a radical of formula II.

Particularly preferred cyanoguanidines are those wherein $R^1$ and $R^2$ are each independently of the other $C_3$-$C_4$alkyl, $C_3$-$C_4$alkenyl, cyclohexyl, phenyl, tolyl, methoxyphenyl, ethoxyphenyl, dichlorophenyl, benzyl, naphthyl or a group of formula II, wherein T is an oxygen atom and R is phenyl or dichloropyridyl.

The radicals $R^1$ and $R^2$ in the compounds of formula I may be different or, preferably, identical.

Particularly suitable cyanoguanidines are those wherein $R^1$ and $R^2$ are each isopropyl, allyl or, preferably, phenyl, as well as a cyanoguanidine of formula I, wherein $R^1$ is phenyl and $R^2$ is allyl.

As already mentioned, the cyanoguanidines present in the compositions of this invention can be prepared by reacting carbodiimides of formula III with cyanamide. If desired, the reaction is carried out in the presence of a basic catalyst, for example a tertiary amine such as triethylamine, in an inert solvent such as 1,2-dichloroethane, diethyl ethyl, tetrahydrofuran, dioxane or, preferably, in a protic solvent such as isopropanol, at room temperature or elevated temperature.

The carbodiimides of formula III are known and can be prepared in known manner, for example from N,N'-disubstituted ureas or thioureas or from isocyanates. Suitable methods of synthesis are described, for example, by S. R. Sandler and W. Karo in "Organic Functional Group Preparation", Vol. 2 (Organic Chemistry Series Vol. 12-2), Academic Press, Orlando, FL, USA, 1986, pp. 233–258.

It will be readily understood that the cyanoguanidine component (b) of the compositions of this invention may consist of only one or also of two or more compounds of formula I. If, for example, component (b) consists of two or more compounds of formula I, then these cyanoguanidine mixtures can be obtained by mixing two or more pure substances or can also be prepared direct as mixtures. A particularly suitable method of preparing such mixtures is, for example, the reaction of two different isocyanates R'—NCO and R"—NCO to give the corresponding carbodiimide mixture containing R'—N=C=N—R', R'—N=C=N—R" and R"—N=C=N—R", and subsequently reacting the resultant carbodiimide mixture with cyanamide. For specific applications it is preferred to use such cyanoguanidine mixtures as hardener, as they generally have better solubility in suitable solvents.

Suitable expoxy resins (a) in the compositions of this invention are all those which can be cured with the cyanoguanidines defined herein. Such epoxy resins are for example:

alicyclic polyepoxides such as epoxyethyl-3,4-epoxycyclohexane (vinylcyclohexene diepoxide), limonene diepoxide, dicyclopentadiene diepoxide, bis(3,4-epoxycyclohexylmethyl)adipate, 3',4'-epoxycyclohexylmethyl-3,4-epoxycyclohexane carboxylate, 3',4'-epoxy-6'-methylcyclohexylmethyl-3,4-epoxy-6-methylcyclohexane carboxylate, 3-(3',4'-epoxycyclohexyl)-2,4-dioxaspiro[5,5]-8,9-epoxyundecane, 3-glycidyloxyethoxyethyl-2,4-dioxaspiro[5,5]-8,9-epoxyundecane;

di- or polyglycidyl ethers of polyhydric alcohols such as 1,4-butanediol or of polyalkylene glycols such as polypropylene glycols, di- or polyglycidyl ethers of cycloaliphatic polyols such as 2,2-bis(4-hydroxycyclohexyl)propane, di- or polyglycidyl ethers of polyhydric phenols such as resorcinol, bis(p-hydroxyphenyl)methane (bisphenol F), 2,2-bis(p-hydroxyphenyl)propane (bisphenol A), 2,2-bis(4'-hydroxy-3',5'-dibromophenyl)propane, 1,1,2,2-tetrakis(p-hydroxyphenyl)ethane, or of condensation products of phenols with formaldehyde, e.g. phenol and cresol novolaks, which condensation products are obtained under acid conditions; and also di- or poly($\beta$-methylglycidyl)ethers of the above polyalcohols and polyphenols;

polyglycidyl esters and poly($\beta$-methylglycidyl)esters of polyvalent carboxylic acids such as phthalic acid, terephthalic acid, tetrahydrophthalic acid and hexahydrophthalic acid;

N-glycidyl derivatives of amines, amides and heterocyclic nitrogen bases, e.g. N,N-diglycidylaniline, N,N-diglycidyltoluidine, N,N,N',N'-tetraglycidyl-bis(p-aminophenyl)methane, triglycidylisocyanurate, N,N'-diglycidylethyleneurea, N,N'-diglycidyl-5,5-dimethylhydantoin, N,N'-diglycidyl-5,5-dimethyl-6-isopropyl-5,6-dihydrouracil.

Preferred epoxy resins (a) are polyglycidyl derivatives of aromatic heterocyclic aromatic compounds, in particular polyglycidyl ethers of bisphenols such as 2,2-bis(4'-hydroxyphenyl)propane (bisphenol A) or bis(4-hydroxyphenyl)methane (bisphenol F).

Mixtures of different epoxy resins may, of course, also be used as component (a). Component (a) preferably contains no epoxy resins which are modified with elastomers.

If desired, active diluents can be added to the curable compositions in order to reduce the viscosity. Examples of such diluents are: styrene oxide, butyl glycidyl ether, 2,2,4-trimethylpentyl glycidyl ether, phenyl glycidyl ether, cresyl glycidyl ether, glycidyl esters of synthetic, highly branched, mainly tertiary, aliphatic monocarboxylic acids.

While the curable mixtures of this invention may contain further conventional hardeners for epoxy resins in addition to the cyanoguanidines of formula I, mixtures which do not contain any additional hardeners, especially those which contain no polyether-polyamines, are preferred.

In addition, curing accelerators can be used in the curing. Examples of such accelerators are: tertiary amines, the salts or quaternary ammonium compounds thereof, e.g. benzyldimethylamine, 2,4,6-tris(dimethylaminomethyl)phenol, 1-methylimidazole, 2-ethyl-4-methylimidazole, 4-aminopyridine, tripentylammonium phenolate; or alkali metal alcoholates, e.g. sodium hexane triolate. The compositions of this invention preferably contain no substituted guanidines as curing accelerators.

Compositions of this invention are preferred which, in addition to containing components (a) and (b), contain a curing accelerator (c), preferably an imidazole derivative.

The components (a), (b) and (c) employed in the compositions of this invention may be individual compounds or mixtures.

The curable compositions of this invention preferably contain 5 to 30% by weight, most preferably 10 to 20% by weight, of component (b) and, optionally, 0.05 to 5% by weight, preferably 0.1 to 1% by weight, of the accelerator (c), based on the amount of (a)+(b).

The invention further relates to the use of the curable compositions for the preparation of crosslinked products.

Curing of the mixtures of the invention is conveniently carried out in the temperature range from 100° to 300° C., preferably from 120° to 250° C. Curing can be carried out in known manner in two or more steps, the first curing step being effected at low temperature and the post-curing at more elevated temperature.

If desired, curing can be carried out in two steps such that the curing reaction is first prematurely discontinued or the first step is carried out at slightly elevated temperature to give a still fusible and/or soluble curable precondensate (B-stage) from the epoxy component (a) and the hardener (b). Such a precondensate can be used, for example, moulding compounds or fluidized powders.

The term "curing" as employed herein means the conversion of the soluble, either liquid or fusible polyepoxide into solid, insoluble and infusible three-dimensional crosslinked products or moulding materials, normally accompanied by simultaneous shaping to moulded articles such as castings, mouldings and laminated materials, and to impregnations, coatings, films or bonds.

The compositions of this invention are particularly suitable for use as laminating resins for the preparation of prepregs and fibre-reinforced composites.

The following Examples illustrate the invention in more detail.

EXAMPLE 1

N-cyano-N'-(2,6-diisopropyl-4-phenoxyphenyl)-N"-tert-butylguanidine 0.46 g of cyanamide are added to a solution of 3.5 g of N-(2,6-diisopropyl-4-phenoxyphenyl)-N'-tert-butylcarbodiimide [prepared in accordance with Example 1 (compound 4) of European patent application A-175 649] in 20 ml of 1,2-dichloroethane. The reaction mixture is refluxed for 21 hours and then concentrated by evaporation to a suspension. This concentrated suspension is stirred with diethyl ether and the crystalline product so obtained is filtered with suction. Melting point 206°–207° C. (recrystallisation from diethyl ether/hexane).

EXAMPLE 2

N-cyano-N'-[2,6-dimethyl-4-(3',5'-dichloro-2'-pyridyloxy)-phenyl]-N"-tert-butylguanidine A solution of 4.26 g N-[2,6-dimethyl-4-(3',5'-dichloro-2'-pyridyloxy)-phenyl]-N'-tert-butylcarbodiimide [prepared in accordance with Example 1 (compound 149) of EP-A 175 649] in 20 ml of 1,2-dichloroethane is reacted with 0.54 g of cyanamide and the reaction mixture is worked up as described in Example 1. The product is obtained in the form of colourless crystals which melt at 206°–207° C.

EXAMPLE 3

N-cyano-N'-cyclohexyl-N"-phenylguanidin

A solution of 1.8 g N-cyclohexyl-N'-phenylcarbodiimide [prepared in accordance with Tetrahedron Letters 26, 1661 (1985) in 20 ml of 1,2-dichloroethane is reacted with 0.42 g of cyanamide and the reaction mixture is worked up as described in Example 1. The viscous oily crude product is chromatographed on silica gel (elution with a 4:1 mixture of methylene chloride/diethyl ether), affording a crystalline product which melts at 147°–147.5° C. (recrystallisation from ethyl acetate).

EXAMPLE 4

N-cyano-N'-2-methoxycarbonylethyl-N"-phenylguanidine 0.17 g of cyanamide is added to a solution of 0.75 g of N-2-methoxycarbonylethyl-N'-phenylcarbodiimide in 8 ml of 1,2-dichloroethane. The reaction mixture is refluxed for 5 hours and then concentrated under vacuum. The residue is chromatographed on silica gel (elution with a 1:1:1 mixture of methylene chloride/diethyl ether/ethyl acetate), to give a colourless crystalline product which melts at 122.5°–123.5° C.

N-2-Methoxycarbonylethyl-N'-phenylcarbodiimide 1.2 g of 2-chloro-1-methylpyridinium iodide are added at room temperature to a solution of 0.95 g of N-2-methoxycarbonylethyl-N'-phenylthiourea and 0.97 g of triethylamine in 20 ml of acetonitrile. The reaction mixture is stirred for 1 hour and the resultant suspension is concentrated by evaporation. The residue is taken up in pentane and washed with water and brine. The solution is dried over magnesium sulfate, filtered and concentrated under vacuum, to give the product as a faintly yellowish oil.

EXAMPLE 5

N-allyl-N'-cyano-N"-phenylguanidine 0.6 g of N-allyl-N'-phenylcarbodiimide in 8 ml of 1,2-dichloromethane is reacted with 0.17 g cyanamide and the reaction mixture is worked up as described in Example 4. Recrystallisation from diethyl ether yields a colourless crystalline product which melts at 99.5°–100.5° C.

N-Allyl-N'-phenylcarbodiimide 0.77 g of N-allyl-N'-phenylthiourea, 0.97 g of triethylamine und 1.2 g of 2-chloro-1-methylpyridinium iodide are reacted and worked up as described in Example 4. The product is obtained as a pale yellow oil.

EXAMPLE 6

N,N'-bis(allyl)-N"-cyanoguanidine

A solution of 0.7 g N,N'-bis(allyl)carbodiimide in 10 ml of 1,2-dichloroethane is reacted with 0.27 g of cyanamide and the reaction mixture is worked up as described in Example 4. Recrystallisation from diethyl ether yields a crystalline product which melts at 66.5°–67.0° C.

N,N'-Bis(allyl)carbodiimide 1.56 g of N,N'-bis(allyl)thiourea, 2.4 g of triethylamine and 3.07 g of 2-chloro-1-methylpyridinium iodide are reacted in 40 ml of acetonitrile and the reaction mixture is worked up as described in Example 4. The product is obtained as a faintly yellowish oil.

EXAMPLE 7

N,N'-bis(1-naphthyl)-N"-cyanoguanidine

A 500 ml three-necked round flask equipped with stirrer, thermometer, reflux condenser as well as drying tube and bubble counter, is charged with:
  126.9 g (0.75 mol) of 1-naphthyl isocyanate
  0.5 g (2.60 mmol) of 3-methyl-1-phenyl-1-phospha-3-cyclopentene-1-oxide, and
  200 ml of toluene.

The solution is stirred for 2 hours under reflux, with evolution of $CO_2$. The solvent is then removed on a rotary evaporator and to the residue (yellowish oil) are added:

250 ml of isopropanol
10 ml of triethylamine, and
31.5 g (0.75 mol) of cyanamide (in portions over 15 minutes).

The reaction mixture is stirred for 2 hours at 70°–80° C., then cooled with an ice bath to ca. 10° C. The precipitate is isolated by filtration, washed with isopropanol and dried under vacuum, affording 124 g (98% of theory) of a colourless powder which melts at 224°–225° C.

Elemental analysis: Calculated (%): C 78.5 H 4.8 N 16.7; Found: C 77.7 H 4.9 N 17.4.

EXAMPLES 8–12

The following compounds are prepared in accordance with the process described in Example 7:

| Example | Compound | Yield (%) | m.p. (°C.) | Elemental analysis (%) (calc./found) | $^1$H—NMR (DMSO—$d_6$: ppm rel. to TMS) |
|---|---|---|---|---|---|
| 8 | (diphenyl cyanoguanidine) | 95 | 198–199 | C 71.2/71.0<br>H 5.1/5.2<br>N 23.7/23.8 | 7.19–7.34 (m, 10 H);<br>9.47 (s, 2 H) |
| 9 | (bis(4-methoxyphenyl) cyanoguanidine) | 98 | 196–197 | C 64.8/64.5<br>H 5.4/5.4<br>N 18.9/19.1 | 3.73 (s, 6 H, OCH$_3$);<br>6.9 und 7.2<br>AA'BB' system 8 H);<br>8.97 (s, 2 H) |
| 10 | (bis(3,4-dichlorophenyl) cyanoguanidine) | 61 | 197–198 | C 44.9/44.9<br>H 2.2/2.3<br>N 15.0/15.0<br>Cl 37.9/37.5 | |
| 11 | (bis(2-methoxyphenyl) cyanoguanidine) | 86 | 170–172 | | |
| 12 | (bis(4-ethoxyphenyl) cyanoguanidine) | 81 | 187–188 | C 66.7/66.6<br>H 6.2/6.3<br>N 17.3/17.5 | |

EXAMPLE 13

N,N'-bis(cyclohexyl)-N''-cyanoguanidine

A 1.5 liter sulfonating flask equipped with stirrer, thermometer, reflux condenser and drying tube is charged with:
206.2 g (1,0 mol) N,N'-dicyclohexylcarbodiimide
500 ml of isopropanol, and
10 ml of triethylamine.

With stirring, 84.1 g (2.0 mol) of cyanamide are added, in portions, over ca. 15 minutes at room temperature. The reaction mixture is then stirred for 2 hours at 70°-80° C. and cooled with an ice bath to ca. 10° C. The precipitate is isolated by filtration, washed with isopropanol and dried under vacuum, affording 190 g (77% of theory) of colourless crystals with a melting point of 191° C.

Elemental analysis: Calculated (%): C 67.7 H 9.7 N 22.6; Found: C 67.7 H 9.7 N 22.6.

EXAMPLES 14-17

The compounds listed in the Table are prepared in accordance with the process described in Example 13. The corresponding carbodiimides are known and can be prepared in known manner.

| Example | Compound | Yield (%) | m.p. (°C.) | Elemental analysis (%) (calc./found) | $^1$H—NMR, (DMSO—$d_6$: ppm rel. to TMS) |
|---|---|---|---|---|---|
| 14 | ⟩—NH—C(=N—CN)—NH—⟨ | 82 | 183-186 | C 57.1/55.8 H 9.6/9.5 N 33.3/34.5 | 1.10 (d, 12 H); 3.77-3.98 (m, 2 H); 6.32 (m, 2 H) |
| 15 | ∼∼—NH—C(=N—CN)—NH—∼∼ | 89 | 60-63 | C 61.2/60.5 H 10.3/10.0 N 28.5/28.1 | 0.8-1.07 (m, 6 H); 1.09-1.57 (m, 8 H); 3.00-3.18 (m, 4 H); 6.78-6.89 (m, 2 H) |
| 16 | Ph-CH₂—NH—C(=N—CN)—NH—CH₂-Ph | 82 | 124-126 | | 4.36 (d, 4 H); 7.15-7.34 (m, 10 H); 7.56-7.69 (m, 2 H) |
| 17 | ⟩—NH—C(=N—CN)—NH—⟨ | 95 | 142-144 | C 61.5/61.1 H 10.3/10.3 N 28.5/28.5 | 0.83 (t, 6 H); 1.07 (d, 6 H); 1.31-170 (m, 4 H); 3.35-3.83 (m, 2 H); 6.34-6.43 (m, 2 H) |

EXAMPLE 18

Preparation of a mixture of cyanoguanidines starting from equimolar amounts of phenyl isocyanate and 4-methoxyphenyl isocyanate Equimolar amounts of phenyl isocyanate and 4-methoxyphenyl isocyanate are reacted to the corresponding cyanoguanidine mixture in accordance with the process described in Example 7. The product so obtained has a melting range of 150°-158° C.

USE EXAMPLES 100 g mixtures are prepared with the respective amounts of the cyanoguanidines indicated in the Table and bisphenol A diglycidyl ether (epoxy value: 5.4 eq/kg) and cured for 4 hours at 180° C. Clear castings are obtained with the glass transition temperatures listed in the Table (Tg, determined by DSC).

| Use Examples | Cyanoguanidine according to Example (g) | Tg (°C.) |
|---|---|---|
| $A_1$ | 7 (20) | 145 |
| $A_2$ | 8 (15) | 145 |
| $A_3$ | 9 (20) | 139 |
| $A_4$ | 13 (15) | 129 |
| $A_5$ | 14 (10) | 140 |
| $A_6$ | 18 (20) | 130 |

-continued

| Use Examples | Cyanoguanidine according to Example (g) | Tg (°C.) |
|---|---|---|
| $A_7$ | 1 (20) | 125 |
| $A_8$ | 2 (20) | 92 |
| $A_9$ | 3 (15) | 110 |
| $A_{10}$ | 4 (15) | 122 |
| $A_{11}$ | 5 (15) | 116 |
| $A_{12}$ | 6 (10) | 90 |

What is claimed is:

1. A curable composition containing
(a) an epoxy resin and
(b) as hardener for the epoxy resin, a cyanoguanidine of formula I

$$R^1-NH-C(=N-CN)-NH-R^2, \quad (I)$$

wherein $R^1$ and $R^2$ are each independently of the other $C_1$-$C_{12}$alkyl, $C_2$-$C_{12}$alkenyl, $C_5$-$C_{10}$cycloalkyl, $C_6$-$C_{10}$aryl or $C_7$-$C_{12}$aralkyl, or are a heterocyclic radical of 4 to 8 carbon atoms or a group of formula II

$$R-T-\text{(phenyl)} \quad (II)$$

wherein R is phenyl or a heterocyclic radical of 4 to 5 carbon atoms, and T is methylene, isopropylidene, CO, O, S or $SO_2$, which radicals $R^1$ and $R^2$ are unsubstituted or substituted by $C_1$-$C_4$alkyl, $C_1$-$C_4$alkoxy, nitro, halogen, $R^3$OCO or $R^3$COO, where $R^3$ is phenyl or $C_1$-$C_4$alkyl.

2. A composition according to claim 1, wherein $R^1$ and $R^2$ are each independently of the other $C_1$-$C_6$alkyl, $C_2$-$C_6$alkenyl, $C_5$-$C_6$cycloalkyl, $C_6$-$C_{10}$aryl, benzyl, or a radical of formula II.

3. A composition according to claim 1, wherein wherein $R^1$ and $R^2$ are each independently of the other $C_3$-$C_4$alkyl, $C_3$-$C_4$alkenyl, cyclohexyl, phenyl, tolyl, methoxyphenyl, ethoxyphenyl, dichlorophenyl, benzyl, naphthyl or a group of formula II, wherein T is an oxygen atom and R is phenyl or dichloropyridyl.

4. A composition according to claim 1, wherein $R^1$ and $R^2$ are identical.

5. A composition according to claim 4, wherein $R^1$ and $R^2$ are phenyl, isopropyl or allyl.

6. A composition according to claim 1, wherein $R^1$ is phenyl and $R^2$ is allyl.

7. A composition according to claim 1, wherein the cyanoguanidine component (b) is a mixture of two or more compounds of formula I.

8. A composition according to claim 1, wherein the epoxy resin (a) is a polyglycidyl derivative of an aromatic or heterocyclic aromatic compound.

9. A composition according to claim 8, wherein the component (a) is a polyglycidyl ether of 2,2-bis(4'-hydroxyphenyl)propane or bis(4-hydroxyphenyl)methane.

10. A composition according to claim 1, which additionally contains a curing accelerator (c).

11. A composition according to either claim 1, which contains 5–30% by weight or the cyanoguanidine (b) and, optionally, 0.05–5% by weight of the accelerator (c), based on the amount of (a)+(b).

12. Method of use of the composition as claimed in claim 1 for the preparation of crosslinked products.

13. Method of use of the composition as claimed in claim 1 as laminating resin for the preparation of prepregs and fibre-reinforced composites.

* * * * *